(12) United States Patent
Frazier

(10) Patent No.: US 7,392,908 B2
(45) Date of Patent: Jul. 1, 2008

(54) METHODS AND APPARATUS FOR SORTING PARTICLES HYDRAULICALLY

(75) Inventor: Erich Frazier, Fort Lauderdale, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 171 days.

(21) Appl. No.: 11/034,396

(22) Filed: Jan. 12, 2005

(65) Prior Publication Data

US 2006/0180517 A1  Aug. 17, 2006

(51) Int. Cl.
*B07C 5/02* (2006.01)
(52) U.S. Cl. ............................ 209/3.1; 209/552
(58) Field of Classification Search ................ 209/3.1, 209/3.2, 155, 552, 576, 906
See application file for complete search history.

(56) References Cited

U.S. PATENT DOCUMENTS

| | | | |
|---|---|---|---|
| 3,560,754 A * | 2/1971 | Kamentsky | ............... 209/559 |
| 3,710,933 A | 1/1973 | Fulwyler et al. | |
| 3,761,941 A | 9/1973 | Robertson | |
| 3,826,364 A | 7/1974 | Bonner et al. | |
| 3,836,912 A | 9/1974 | Ghougasian et al. | |
| 3,878,519 A | 4/1975 | Eaton | |
| 3,953,860 A | 4/1976 | Fujimoto et al. | |
| 3,963,606 A | 6/1976 | Hogg | |
| 3,982,251 A | 9/1976 | Hochberg | |
| 4,025,926 A | 5/1977 | Fujimoto et al. | |
| 4,045,770 A | 8/1977 | Arnold et al. | |
| 4,047,143 A | 9/1977 | Burden et al. | |
| 4,325,483 A | 4/1982 | Lombardo et al. | |
| 4,756,427 A * | 7/1988 | Gohde et al. | ............... 209/3.1 |
| 5,101,978 A * | 4/1992 | Marcus | ............... 209/3.1 |
| 5,180,065 A * | 1/1993 | Touge et al. | ............... 209/577 |
| 5,528,045 A | 6/1996 | Hoffman et al. | |
| 6,228,652 B1 | 5/2001 | Rodriguez et al. | |
| 6,382,228 B1 * | 5/2002 | Cabuz et al. | ............... 137/10 |
| 6,994,218 B2 * | 2/2006 | Kawano et al. | ............... 209/210 |
| 2003/0027225 A1 * | 2/2003 | Wada et al. | ............... 435/7.21 |

* cited by examiner

*Primary Examiner*—Joseph C Rodriguez
(74) *Attorney, Agent, or Firm*—Warren W. Kurz; Mitchell E. Alter

(57) ABSTRACT

A method and apparatus for selectively sorting individual particles, such as blood cells of a particular type of interest, from a plurality of particles of different types. Particles of interest are individually differentiated from other particles in a known manner, and a discrete control signal is produced in response to having identified a particle of interest. An impulse generator, acting in response to such control signal, applies a focused impulsive force on the identified particle of interest, such force serving to eject such particle from the plurality of particles of which it is a part. The ejected particles of interested are then collected in a separate container. The apparatus of the invention is preferably embodied in a flow cytometric instrument.

8 Claims, 5 Drawing Sheets

METHODS AND APPARATUS FOR SORTING
PARTICLES HYDRAULICALLY

BACKGROUND OF THE INVENTION

1. Field of the Invention

The present invention relates to improvements in methods and apparatus of the type commonly used to automatically and rapidly sort minute particles, e.g. biological cells, entrained in a moving liquid on the basis of certain predetermined particle characteristics. More particularly, it relates to a particle-sorting method and apparatus in which particles of interest are selectively extracted from their entraining liquid by using a hydraulic impulse to selectively eject such particles of interest from the entraining liquid.

2. The Related Prior Art

Flow cytometry is commonly used to differentiate various types of cells and other "formed bodies" comprising a biological fluid, e.g., whole blood. Conventional flow cytometers commonly comprise an optically-transparent flow cell, usually made of quartz, having a central channel through which a stream of cells to be individually identified is made to flow. Movement of the cell stream through the flow cell channel is hydrodynamically entrained to the central longitudinal axis of the flow cell channel by a cell-free sheath liquid that concentrically surrounds the cell stream and flows along with the cell stream as it passes through the flow cell channel. As each cell passes through a cell-interrogation zone of the flow cell channel, it is irradiated with a focused beam of radiation (as commonly provided by a laser source). Upon impinging upon each cell, the laser beam is scattered in a pattern characteristic of the morphology, density, refractive index and size of the cell. Further, the spectral characteristics of the laser beam may act to excite certain fluorochromes associated with selected cells, as may be the case when a cell's DNA has been previously stained with such fluorochromes, or when a fluorochrome molecule has been previously conjugated with a selected type of cell, either directly or via an intermediate bead or the like. Photodetectors strategically positioned about the optical flow cell serve to convert the light-scattered by each cell and the fluorescence emitted by the excited fluorochromes to electrical signals which, when suitably processed, serve to identify the irradiated cell. In addition to the light scatter and fluorescence measurements made on each cell, some flow cytometers further characterize each cell by measuring certain physical and/or electrical properties of each cell as it passes through the flow cell. Using the well-known Coulter Principle, a DC and/or an RF current is caused to pass through a constricted aperture in the flow cell channel simultaneously with the movement of cells therethrough. The volume of each cell affects the level of DC current through the flow cell aperture, and the cell's electrical conductivity affects the RF current through such aperture. See, for example, the flow cytometer disclosed in the commonly assigned U.S. Pat. No. 6,228,652, issued in the names of Carlos M. Rodriguez et al.

A conventional light scatter and fluorescence-sensing flow cytometer of the type noted above is disclosed in U.S. Pat. No. 3,710,933 issued to Mack J. Fulwyler et al. To this standard flow cytometer, Fulwyler et al. have added a cell-sorting component that operates to selectively remove and collect certain cells of interest (e.g., abnormal cells) from the effluent of cells that have already passed through the optical flow cell and have been identified as to cell type. More specifically, the cell-sorting component comprises a piezoelectric device that acts to vibrate the flow cell so as to effect the production a stream of droplets from the cell-entraining sheath liquid exiting from the flow cell. Ideally, each droplet contains but a single cell that has been characterized as to cell type by the light-scatter and fluorescence measurements just made on such cell. Each droplet in the droplet stream is then electrostatically charged as it passes between a pair of electrically charged plates, and each charged droplet is selectively deflected (or not deflected) towards a collection container as it passes between a pair of electrostatically charged deflection plates, such plates being charged to a droplet-deflecting polarity only at a time to deflect droplets (and cells) of interest. The instantaneous polarity of the deflection plates is determined by a cell-characterization processor that processes the cell-measurement signals from the optical flow cell.

In cell-sorting flow cytometers of the above type, the continuous production of suitably sized droplets can be problematic. Not only is it technically difficult to continuously produce droplets that contain only a single cell, but also the required size of the droplets is so small (aerosol in size) that it is difficult to control their precise movement as they exit from the flow cell. Typically, when it is suspected that a droplet contains more than one cell, the droplet is allowed to proceed to a waste container in order to avoid potential contamination of the collected cells of interest with other cells.

SUMMARY OF THE INVENTION

In view of the foregoing discussion, an object of this invention is to provide an improved particle-sorting apparatus and method that overcomes the above-described technical problems of the prior art technique.

According to a first aspect of the invention a new and improved method is provided for selectively sorting particles of a particular type of interest from a plurality of particles of different types, including particles of the particular type of interest. Such method generally comprises the steps of: (a) differentiating individual particles of the particular type of interest from other particles in the plurality of particles, and producing a discrete control signal corresponding to the differentiation of each particle of the particular type of interest; (b) selectively producing, in timed relation to the production of each control signal, an impulsive physical force on a specific particle in the plurality of particles whose differentiation has resulted in the production of the corresponding control signal, such impulsive physical force being adapted to eject only such specific particle from the plurality of particles; and (c) collecting the individual particles ejected from the plurality of particles in a separate container. According to a preferred embodiment, the plurality of particles are contained in a liquid medium, and the impulsive physical force is a focused hydraulic force that is applied to a particle of interest within the liquid medium. In a particularly preferred embodiment, the plurality of different particles is entrained as a linear array in a moving stream of liquid. In this case, the particles are characterized as to type, one after another, as they pass a fixed location along the path of the entraining liquid stream. The focused hydraulic force is applied to the entraining liquid at a second location downstream of the fixed location at which each particle is characterized, and in timed relationship to the passage of a particle of interest past such second location. The focused hydraulic force operates to expel a droplet of liquid from the particle-entraining liquid, each droplet so produced containing a particle of interest. Preferably, the method of the invention is carried out in a flow cytometric instrument of the type described herein.

According to a second aspect of the invention, an improved apparatus is provided for selectively sorting particles of a particular type of interest from a plurality of particles of different types, including particles of the particular type of interest. Such apparatus generally comprises (a) a particle-characterizing component, such as the optical flow cell and its associated particle-detecting components of a conventional flow cytometer, for differentiating individual particles of interest from other types of particles within the plurality of particles, and for producing a control signal in response to having differentiated a particle of interest; (b) an impulse generator operatively coupled to the particle-characterizing component and responsive to a control signal produced thereby to produce a focused physical force adapted to eject a single particle of interest from the plurality of particles of different types; and (c) a container for collecting such ejected particles. Preferably, the impulse generator is a piezo-electrically driven device that operates to provide a focused hydraulic impulse (i.e., a short-lived force) on a moving stream of liquid serving to entrain particles moving along a desired path. Such impulse is timed to eject a liquid droplet from the moving stream of liquid, such droplet containing a particle of interest.

The particle-sorting method and apparatus of the invention are advantageous over the afore-described electrostatic particle-sorting technique in that there is no need for an electrostatic deflection mechanism and circuitry for electrostatically charging and selectively deflecting particle-containing droplets as a means to sort particles. Thus, the costs of such components are eliminated, as are the attendant disadvantages noted above. In the particle-sorting method of the invention, the only droplets that are formed are those containing the particles of interest. Thus, there is no undesirable aerosol of droplets containing particles of no interest.

The invention and its advantages will be better understood from the ensuing detailed description of preferred embodiments, reference being made to the accompanying drawings in which like reference characters denote like parts.

BRIEF DESCRIPION OF THE DRAWINGS

DETAILED DESCRIPTION OF PREFERRED EMBODIMENTS

Figure 1:
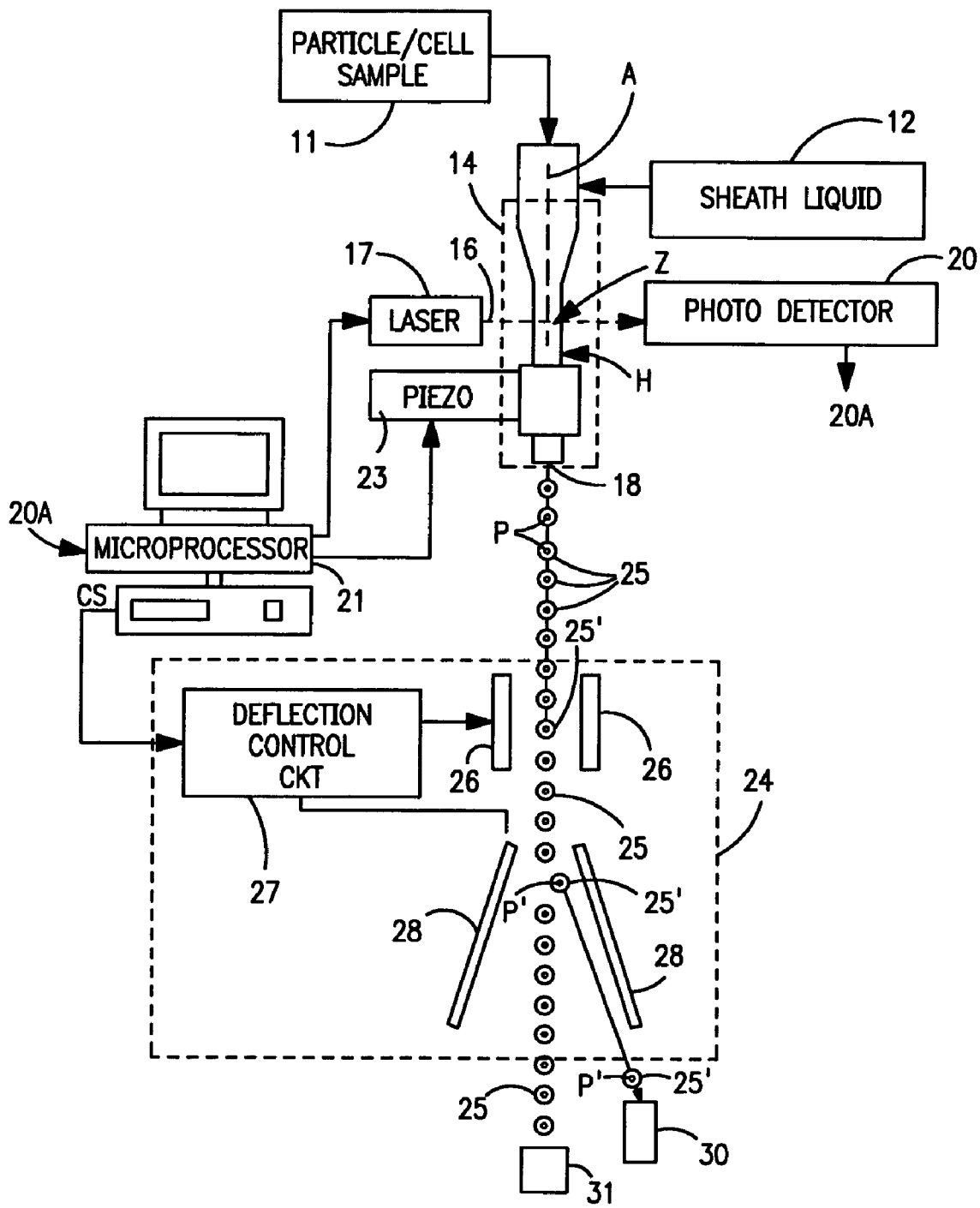
FIG. 1 is a schematic illustration of a prior art system for sorting particles of different types.

Referring now to the drawings, FIG. 1 illustrates a conventional particle-sorting flow cytometer of the type described above. Briefly, particles to be analyzed and sorted, such as cells of a centrifuged blood sample stored in a container 1, are injected into a pressurized stream of sheath liquid e.g., saline) provided from a source 12. The sheath liquid concentrically surrounds the injected particles and causes the particles to travel along the central longitudinal axis A of an optical flow cell 14. The particles to be analyzed are introduced into the sheath fluid at a rate such that the particles are spaced apart and pass one-at-a-time through the flow cell as a substantially linear array of particles. The flow cell is fabricated from an optically transparent material, typically quartz. As each particle passes through the flow cell, it passes through an interrogation zone Z where it is irradiated by a beam of radiation 16, commonly provided by one or more continuous-wave lasers 17. Beam radiation, as modulated by each of the irradiated particles, and/or fluorescent radiation emitted by the irradiated particles, is detected by an array of photodetectors 20. Some of the individual photodetectors serve to detect light scatter in the forward and side directions, while others serve to detect fluorescence. The respective photodetector outputs 20A are then processed, in a well-known manner, by a microprocessor-controlled work station 21 to provide a characteristic signature that identifies the type of each particle irradiated. Having identified a particle type, the work station provides a control signal CS to an electrostatic sorting system 24 which operates to sort particles of different types in different containers 30, 31.

In order to isolate (sort) particles of a particular type from other particles in the sample as they exit the flow cell, a portion of the housing H of the flow cell is vibrated at high frequency by a piezoelectric driver 23 or the like. The effect of such vibration is to cause the stream of sheath liquid exiting the flow cell through a nozzle 18 to break-up into individual droplets 25, each droplet containing only a single particle P of the sample. The electrostatic sorting system 24 operates in a known manner to selectively deflect, by electrostatic forces, droplets of interest, i.e., those droplets containing particles P' of interest, into a receptacle 30, while the majority of droplets are collected in a waste receptacle 31. The electrostatic sorting system 24 comprises a pair droplet-charging electrodes 26 positioned downstream of the discharge nozzle 18, on opposite sides of the path of the droplet stream. Electrodes 26 operate under the control of a control circuit 27 and workstation 21 to charge only those droplets containing a particle P' of interest, as determined by the processed output of the photodetectors 20. The remaining droplets remain uncharged. Of course, the application of the electrostatic charge to a droplet of interest is timed to coincide with the passage of such droplet past the charging electrodes. A pair of charged deflection plates 28 positioned down-stream of the charging electrodes 26 serves to deflect only the charged droplets 25' into receptacle 30.

As noted earlier herein, the electrostatic particle-sorting component of the above-described sorting flow cytometer is problematic in certain respects. Most notably, it requires that every particle to be sorted, whether of interest or not, must be contained in a tiny droplet of a size that can be readily deflected from its normal direction of movement by electrostatic forces. Ideally, only those particles of interest need be confined to such droplets, and the remainder can be propelled directly to waste without any droplet formation. In accordance with the present invention, the electrostatic component of the prior art sorting system has been eliminated in its entirety. In its place, a mechanical particle-sorting mechanism is provided which operates only on the relatively small number of particles of interest (i.e., those particles that are to be separated from the larger mass of other particles in a sample) and allows the remaining particles to proceed along a path without any processing or treatment whatsoever.

Figure 2:
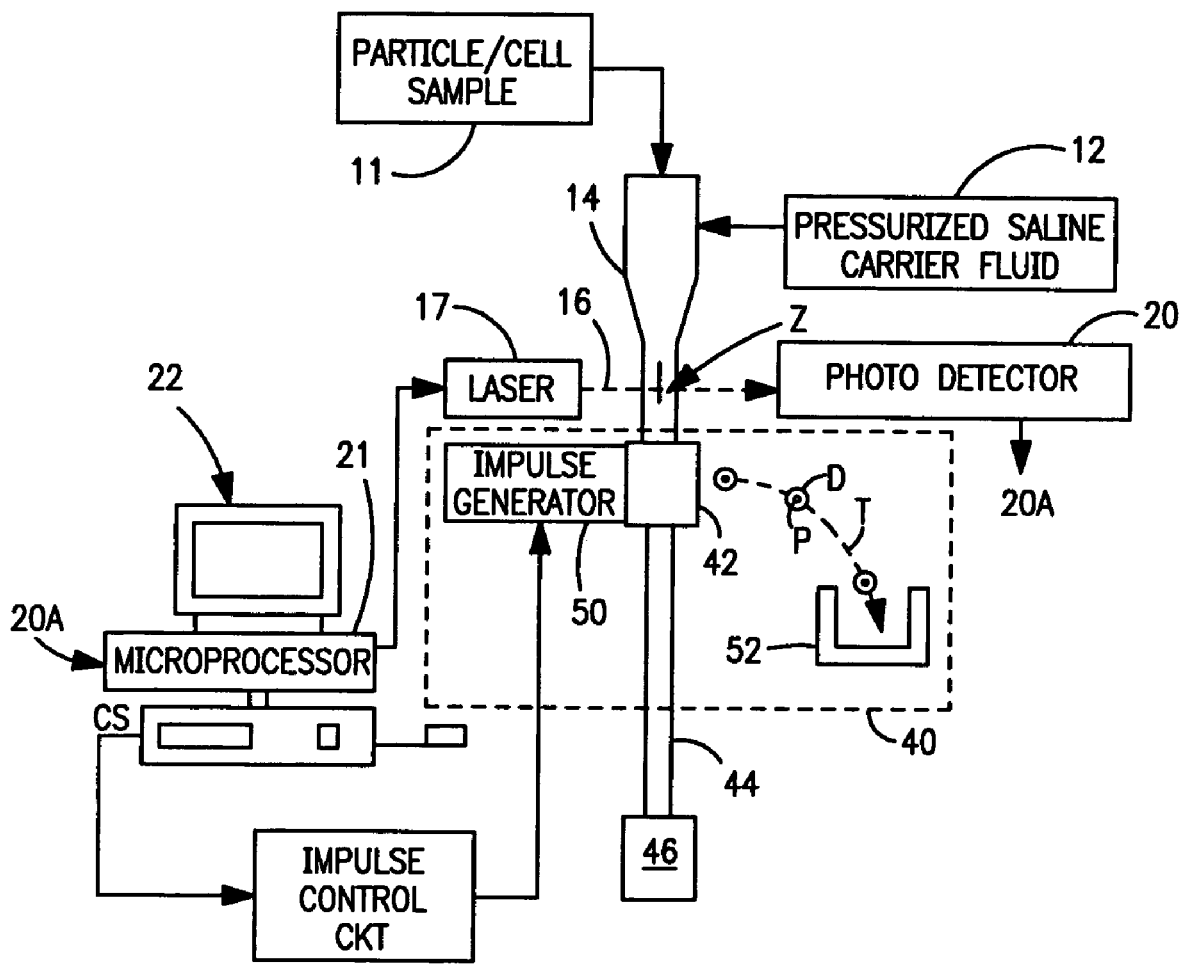
FIG. 2 is a simple timing chart illustrating the time relationship between the detection of a particle and the time at which such particle is sorted by the apparatus of FIG. 1.

Referring to the schematic illustration of FIG. 2, a particle-sorting flow cytometer structured in accordance with a preferred embodiment of the invention comprises an optical flow cell 14 of the general type described above. As in the case of the prior art flow cytometer, particles to be characterized, e.g., blood cells, are provided to an optical flow cell 14 from a source 11, and a particle-entraining sheath liquid is provided to the flow cell from a suitable source 12. As entrained by the sheath liquid, the particles pass, one at a time, through a particle interrogation zone Z where they are irradiated by a laser beam 16, and the scattered radiation and/or fluorescence emanating from the irradiated particle is detected by the photodetector component 20, described above. The outputs of the individual photodetecting elements are processed by the workstation 21 to identify a particle of interest, and a control signal CS. In accordance with the present invention, such control signal is used to control, via an impulse control circuit 41, a sorting mechanism 40 that operates to physically eject (as opposed to electrostatically deflect) the individual particles of interest flowing from the flow cell, and, in doing so, to surround such ejected particle with a droplet of sheath liquid. The non-ejected particles remain in the laminar flow of the sheath liquid which is normally directed to waste.

Figure 3:
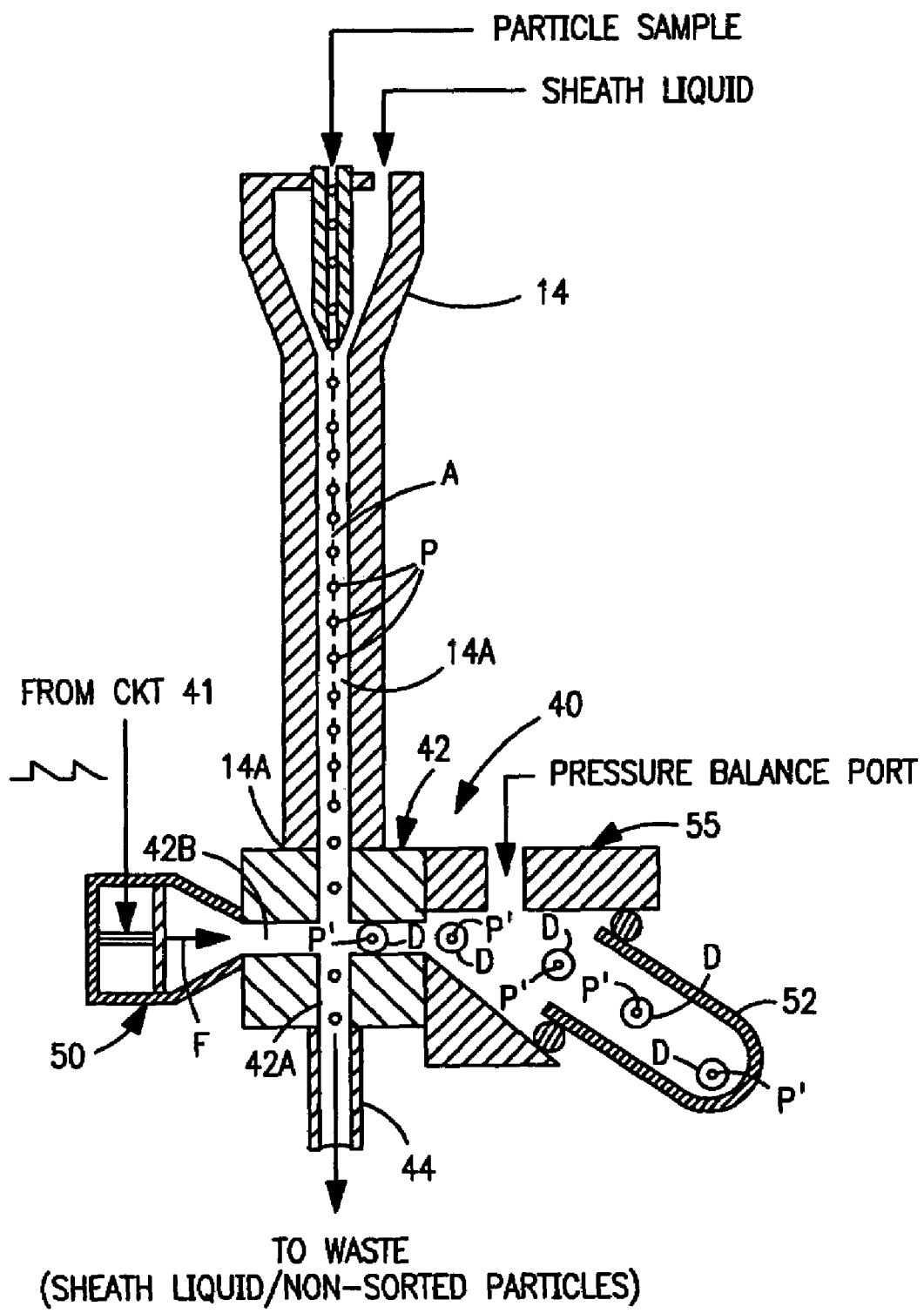
FIG. 3 is an enlarged schematic illustration of a preferred apparatus for sorting particles in accordance with the present invention.

Referring additionally to the schematic illustration of FIG. 3, the above-noted particle-sorting mechanism 40 preferably comprises a flow cell extension element 42 that is affixed, at one end, to the exit end 14A of the flow cell 14 so as to form a liquid-tight seal therewith. The extension element 42 has a central bore 42A having a longitudinal axis that coincides with the central axis A of the flow cell. Further, bore 42A has a size and transverse cross-section selected to match that of the flow cell channel 14A. The opposite end of the extension element is connected to a tube 44 leading to a waste container 46. The flow cell extension member 42 further defines a transverse bore hole 42B that intersects perpendicularly with the central bore 42A. One end of the transverse bore hole 42 communicates with an impulse generator 50, described in detail below, and the opposite end of the transverse bore hole is communicates with a container 52 for collecting the particles of interest. On command, the impulse generator 50 operates to produce a transverse, impulsive (i.e., short-lived) force F that is focused on a selected particle P' positioned at the juncture of bore holes 42A and 42B. As a result of this force, a droplet D of sheath liquid containing such particle to be ejected from the flow cell extension element and follow a trajectory T towards the particle-sorting container 52.

In accordance with a particularly preferred embodiment, each of the bore holes 42A and 42B are circular in transverse cross-section, and each has a diameter of between 150 and 300 microns. Thus, as a result of the pressure pulse applied to the flowing sheath liquid, the size of the droplet surround a particle of interest is of comparable diameter, i.e., between 150 and 300 microns. Preferably, container 52 is supported by a housing 55 connected in an air-tight manner to a lateral side of the extension element 42. Housing 55 defines a pressure-balancing port 56 in which a small pressure-controlling valve (not shown) is inserted to control the pressure within the container 52 and within the exit side of the transverse bore hole 42B. Such pressure control, in combination with the surface tension of the flowing sheath liquid, prevents sheath liquid, other than that from which the droplets D are formed, from exiting from the flow channel 42A through the transverse bore hole 42B in the absence of a pressure pulse from the impulse generator 50.

Figure 4:
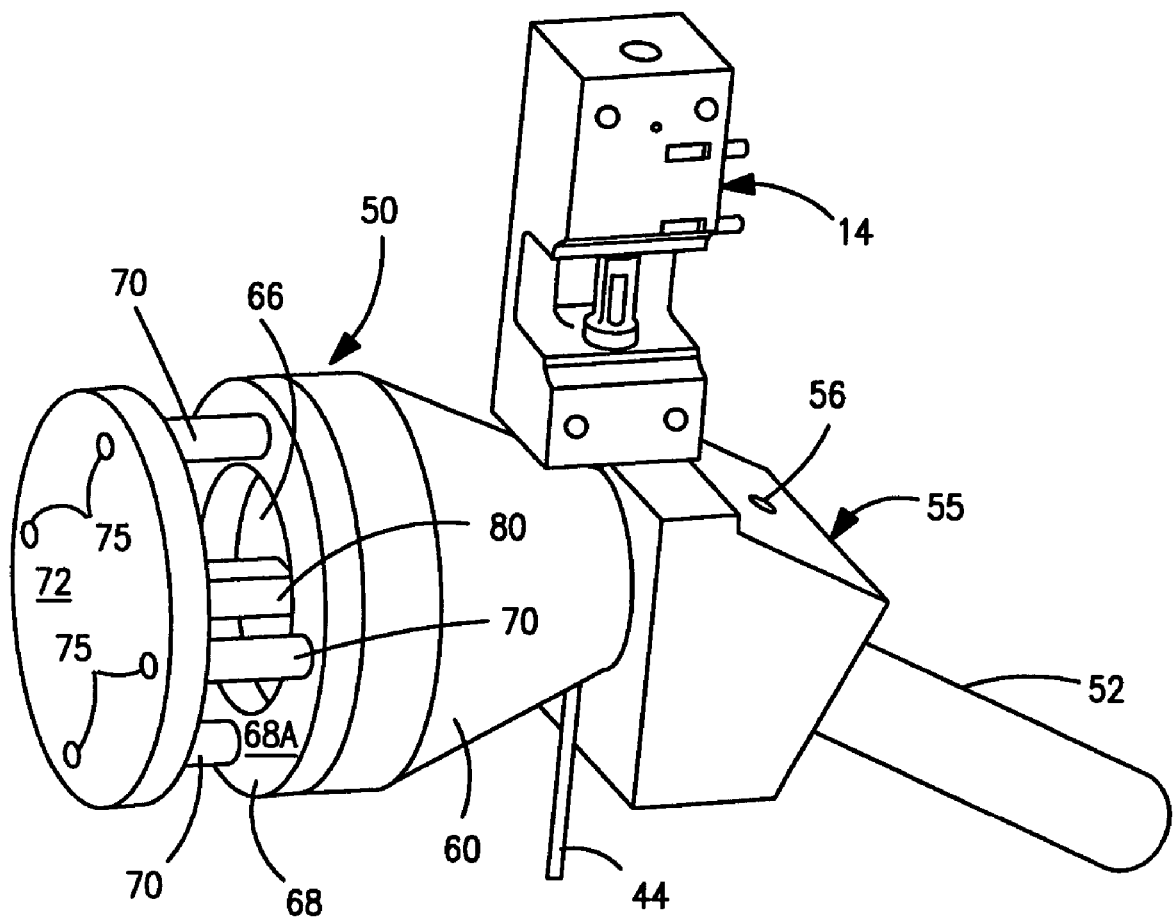
FIGS. 4 and 5 are perspective and cross-sectional illustrations of preferred apparatus of the invention.
Figure 5:
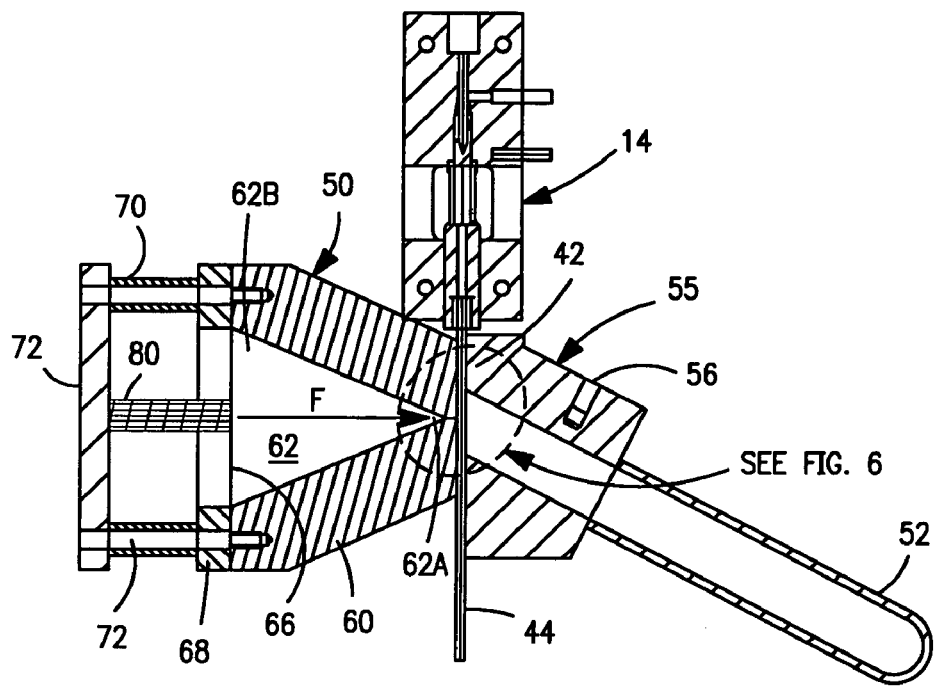
Figure 6:
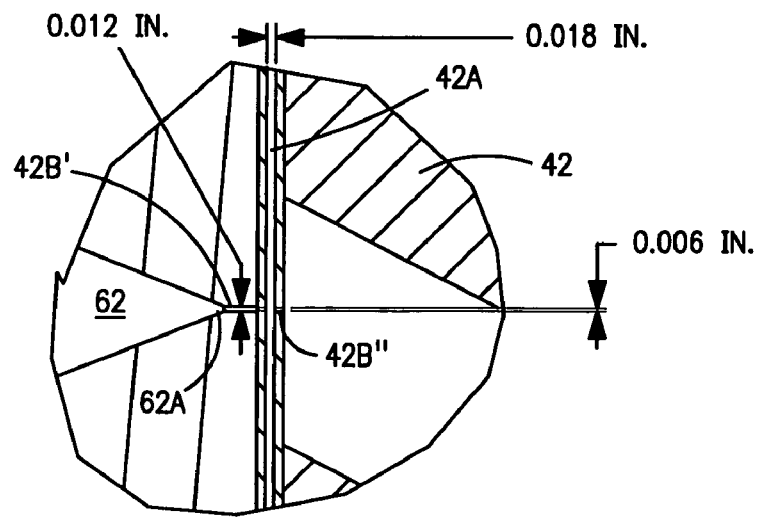
FIG. 6 is an enlarged cross-sectional illustration of a portion of the apparatus shown in FIG. 5.

Referring to FIGS. 4-6 which illustrate the structural details of a preferred impulse generator 50, the latter is shown as comprising a metal (e.g., aluminum) housing 60 that defines a conical pressure chamber 62 within. During operation of the apparatus of the invention, chamber 62 becomes filled with sheath liquid which serves as the medium through which a focused hydraulic force is applied to eject particles of interest from the particle stream flowing through the flow cell extension 42. Preferably, housing 60 is generally conical in shape, as shown in FIG. 4; however, it will be appreciated that it may have any exterior shape whatsoever. At the apex of the conically shaped pressure chamber, the chamber converges towards a small bore hole 64 that communicates with the open end of bore hole 42B formed in the flow cell extension element 42. The details of this arrangement are best shown in FIG. 6. The enlarged open end 62B of chamber 62 is sealed by a thin diaphragm 66, preferably made of stainless steel or brass and having a thickness of about 250 microns (0.010 inch). In the example shown, the open end 62B of the pressure chamber has a diameter of about 36 mm (1.5 inches); thus, diaphragm 66 must have a somewhat larger diameter, preferably about 62.5 mm (2.5 inches), so as to readily cover the pressure chamber opening. The distance between the diaphragm and the apex 62A is of the order of 50 mm. (2.0 inches). The diaphragm is held in place atop the end of housing 60 by a circular metal ring 68. Preferably, ring 68 has an inside diameter that coincides with that of the largest diameter of the conical pressure chamber 62. Ring 68 is held in place atop diaphragm 66 by a plurality of leg members 70 which extend between a rigid metal cover plate 72 and the outer surface of the ring. A stacked piezoelectric beam 80 is positioned in the space between the inside planar surface 72A of the cover plate and the center of the diaphragm. The nominal length of beam 80 is about 25 mm. (1.0 inch). In a known manner, the length of the piezoelectric beam can be selectively increased, e.g., by 25 microns, by the application of a suitable driving voltage across the piezoelectrically-active portion of beam 80. Preferably, the waveform of such driving voltage is in the form of a sawtooth, whereby the beam will rapidly increases in length, followed by a much more gradual return to its nominal length. The relatively sudden increase in beam length causes the nominally planar diaphragm 66 to change shape, becoming convex in the direction from left to right, as viewed in the drawing. The effect of this change in shape is to suddenly reduce the volume of the pressure chamber, thereby producing a focused hydraulic force F (owing to the conical shape of the chamber) on the fluid within the chamber and causing the fluid therein to rapidly exit through the hole 64 formed in the apex of the chamber. The focused hydraulic force so produced will impact that portion of the sheath liquid surround the particle of interest, causing a droplet containing such particle to be ejected from the particle stream and to land in the container 52.

From the enlarged view of FIG. 6, it will be appreciated that the bores 42A and 42B need not be of the same size. As shown, bore hole portion 42B" through which the droplets are ejected from the flow cell extension may be made significantly smaller than the bore hole portion 42B' through which the particle-ejecting hydraulic force is applied. Similarly, bore hole portion 42B' may be significantly smaller that bore hole 42A through which the particle stream and its entraining sheath liquid pass. For example, bore hole portion 42B" may be only 150 microns (0.006 inch) in diameter, while bore hole portion 42B' is 300 microns (0.012 inch) in diameter, and bore hole 42A is 450 microns (0.018 inch) in diameter. The respective bore hole diameters will depend on various system parameters, e.g., the sizes of the particles in the sample, the viscosity of the sheath liquid, etc.

Using the apparatus of the present invention, particles of interest may be sorted at a rate of up to about 1000 particles per second. While this sorting rate is somewhat slower than that which is attainable by the electrostatic sorting method of the prior art, the apparatus of the invention is significantly less complex, and it avoids the already-noted disadvantages of the prior art technique. Further, the apparatus of the invention operates to displace the particles of interest significantly further from the main particle stream than the prior art technique. For example, 150 micron droplets can be easily projected with a velocity such that the droplets travel 10 cm. horizontally before dropping 2.5 cm. vertically. Such a velocity enables the sorting apparatus to be substantially more compact than convention electrostatic sorting devices.

The invention has been described with regard to a preferred embodiment. It will be understood, however, that various modifications and changes may be made without departing from the spirit of the invention, and such variations are intended to fall within the scope of the appended claims.

What is claimed is:

1. A method for selectively sorting individual particles of a particular type of interest from a plurality of particles of different types, including said particles of a particular type of interest, said method comprising the steps of:
    (a) entraining said plurality of particles in a continuous flow of sheath liquid serving to advance said particles, one-at-a-time, along a linear path leading through and beyond an optical flow cell of a flow cytometer in which said individual particles of a particular type of interest are differentiated from other particles within said plurality of particles, and in which a discrete control signal corresponding to the differentiation of each of said individual particles of a particular type of interest is produced, to a location at which said particles are to be sorted;
    (b) selectively producing, in response to the production of each of said control signals, an impulsive hydraulic force that is focused on a specific particle that is located in said plurality of particles entrained in said continuous flow of sheath liquid and whose differentiation has resulted in the production of a corresponding control signal, said impulsive hydraulic force being applied at a location downstream of said optical flow cell and in a direction substantially perpendicular to said linear path, said impulsive hydraulic force being adapted to eject only said specific particle from said plurality of particles moving along said linear path within said continuous flow of sheath liquid and to eject said specific particle, together with a volume of sheath liquid that surrounds such particle as a droplet, in a direction substantially perpendicular to said linear path; and
    (c) collecting the individual particles ejected from said plurality of particles in a separate container.

2. The method as defined by claim 1 wherein said plurality of particles comprises various different cells of a biological liquid sample.

3. The method as defined by claim 2 wherein said biological liquid sample comprises a blood sample, and wherein said plurality of particles comprises different types of blood cells within said blood sample.

4. The method as defined by claim 1 wherein said method is carried out by a flow cytometric instrument.

5. A flow cytometric apparatus for selectively sorting individual particles of a particular type of interest from a plurality of particles of different types, including said particles of a particular type of interest, said apparatus comprising:
    (a) a particle-characterizing component for differentiating said individual particles of a particular type of interest from other types of particles within said plurality of particles, and for producing a control signal in response to having differentiated a specific particle of interest, said component including an optical flow cell through which said plurality of particles are caused to flow, one-at-a-time, along a linear path leading through and beyond said optical flow cell while entrained in a moving continuous stream of sheath of liquid;
    (b) an impulse generator operatively coupled to the particle-characterizing component and responsive to said control signal produced thereby to produce a focused hydraulic force substantially perpendicular to said linear flow path and adapted to impact said continuous stream of sheath liquid at a sorting location downstream of said optical flow cell at which said specific particle of interest is ejected from said plurality of particles of different types flowing along said linear path, together with a volume of sheath liquid that surrounds such particle to form a droplet containing said specific particle, said droplet being ejected, in a direction perpendicular to said linear path; and
    (c) a container for collecting ejected specific particles from said plurality of particles.

6. The apparatus as defined by claim 5 wherein said impulse generator comprises a piezo-electrically-driven device that operates to provide a focused hydraulic impulse on a specific particle entrained in said moving sheath of liquid, said impulse being timed to eject a liquid droplet of said moving sheath of liquid, said droplet containing said specific particle of interest.

7. The apparatus as defined by claim 5 wherein said impulse generator comprises a liquid-containing pressure chamber positioned adjacent said continuous flow of sheath liquid at said sorting location, and an assembly for producing a hydraulic impulse within said chamber that is focused towards a specific cell within said continuous flow of sheath liquid.

8. The apparatus as defined by claim 7 wherein said pressure chamber is conical in shape having a relatively small opening at one end and a relatively large opening at its opposite end, and said assembly comprises a flexible diaphragm covering said large opening, and a piezoelectric beam positioned to selectively deform said diaphragm, whereby a focused hydraulic force is created at said relatively small opening.

* * * * *